United States Patent
Li et al.

(10) Patent No.: US 9,789,473 B2
(45) Date of Patent: Oct. 17, 2017

(54) USE OF CATALYST PREPARED WITH A SUBGROUP VI ELEMENT FOR THE PRODUCTION OF ORGANIC CHEMICALS AND FUELS FROM LIGNIN

(71) Applicant: TIANJIN UNIVERSITY, Tianjin (CN)

(72) Inventors: Yongdan Li, Tianjin (CN); Rui Ma, Tianjin (CN); Xiaolei Ma, Tianjin (CN); Wenyue Hao, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 14/791,999

(22) Filed: Jul. 6, 2015

(65) Prior Publication Data
US 2016/0074843 A1 Mar. 17, 2016

Related U.S. Application Data

(63) Continuation-in-part of application No. PCT/CN2013/090604, filed on Dec. 26, 2013.

(30) Foreign Application Priority Data

Jan. 8, 2013 (CN) .......................... 2013 1 0008112
May 27, 2013 (CN) .......................... 2013 1 0201165
May 27, 2013 (CN) .......................... 2013 1 0201271

(51) Int. Cl.
C07C 1/20 (2006.01)
C07C 37/54 (2006.01)
(Continued)

(52) U.S. Cl.
CPC .............. B01J 27/24 (2013.01); B01J 23/28 (2013.01); B01J 23/88 (2013.01); B01J 23/888 (2013.01);
(Continued)

(58) Field of Classification Search
None
See application file for complete search history.

(56) References Cited

U.S. PATENT DOCUMENTS 3,869,521 A * 3/1975 Benson ..................... B01J 23/36
502/202
4,420,644 A * 12/1983 Huibers .................. C07C 37/54
568/799
(Continued)

FOREIGN PATENT DOCUMENTS

CN 101768052 A 7/2010
CN 102040483 A 5/2011
(Continued)

OTHER PUBLICATIONS

CN102476980A English Translation from Google obtained on Jan. 22, 2016, pp. 1-7.*
(Continued)

*Primary Examiner* — Philip Louie
(74) *Attorney, Agent, or Firm* — Oliff PLC (57) ABSTRACT

A process for the production of organic chemicals and fuels from lignin in the presence of a molybdenum or tungsten based catalyst, comprising mixing the lignin with the catalyst and a solvent in a sealed reactor, introducing an inert gas or hydrogen to the reactor to replace oxygen therein, and heating the sealed reactor to perform a depolymerization reaction at a reaction temperature of above 200° C. to obtain liquid products, which include aromatic compounds, esters, alcohols, monophenols and benzyl alcohols.

6 Claims, 1 Drawing Sheet

(51) Int. Cl.
- *B01J 23/28* (2006.01)
- *B01J 27/19* (2006.01)
- *B01J 27/24* (2006.01)
- *B01J 23/88* (2006.01)
- *B01J 23/888* (2006.01)
- *B01J 23/89* (2006.01)
- *B01J 27/188* (2006.01)
- *B01J 27/22* (2006.01)
- *C07C 29/00* (2006.01)
- *C07C 67/00* (2006.01)

(52) U.S. Cl.
CPC ......... *B01J 23/8993* (2013.01); *B01J 27/188* (2013.01); *B01J 27/19* (2013.01); *B01J 27/22* (2013.01); *C07C 1/20* (2013.01); *C07C 29/00* (2013.01); *C07C 37/54* (2013.01); *C07C 67/00* (2013.01); *C07C 2521/04* (2013.01); *C07C 2521/06* (2013.01); *C07C 2521/08* (2013.01); *C07C 2521/10* (2013.01); *C07C 2521/18* (2013.01); *C07C 2527/188* (2013.01); *C07C 2527/19* (2013.01); *C07C 2527/22* (2013.01); *C07C 2527/24* (2013.01)

(56) References Cited

U.S. PATENT DOCUMENTS

| 4,647,704 | A | 3/1987 | Engel et al. | |
|---|---|---|---|---|
| 4,731,491 | A | 3/1988 | Urban et al. | |
| 2008/0050792 | A1* | 2/2008 | Zmierczak | C10G 1/002 435/161 |
| 2011/0167713 | A1* | 7/2011 | Quignard | C10G 1/08 44/307 |
| 2012/0227966 | A1* | 9/2012 | Dreher, Jr. | E21B 43/243 166/272.3 |
| 2012/0302796 | A1* | 11/2012 | Dhepe | C07C 37/004 568/309 |
| 2013/0030228 | A1* | 1/2013 | Chen | C10G 1/02 585/240 |

FOREIGN PATENT DOCUMENTS

| CN | 102476980 A | 5/2012 |
|---|---|---|
| CN | 103055933 A | 4/2013 |

OTHER PUBLICATIONS

Aegerter, Paul A. et al., "Thiophene Hydrodesulfurization over Alumina-Supported Molybdenum Carbide and Nitride Catalysts: Adsorption Sites, Catalytic Activities, and Nature of the Active Surface," Journal of Catalysis, vol. 164, pp. 109-121 (1996).

Korlann, Scott et al., "Synthesis of Bulk and Alumina-Supported Bimetallic Carbide and Nitride Catalysts," Chemistry of Materials, vol. 14, pp. 4049-4058, (2002).

Miyao, T. et al., "Preparation and Characterization of Alumina-supported Molybdenum Carbide," Applied Catalysis A: General, vol. 165, pp. 419-428, (1997).

Lee, J.S. et al., "Molybdenum Carbide Catalysts," Journal of Catalysis, vol. 125, pp. 157-170, (1990).

Liang, Changhai et al., "Nanostructured beta-Mo2C Prepared by Carbothermal Hydrogen Reduction on Ultrahigh Surface Area Carbon Material," Chemistry of Materials, vol. 14, pp. 3148-3151, (2002).

Stinner, C. et al., "Formation, Structure, and HDN Activity of Unsupported Molybdenum Phosphide," Journal of Catalysis, vol. 191, pp. 438-444, (2000).

Wise, R. S. et al., "Synthesis of High Surface Area Molybdenum Nitride in Mixtures of Nitrogen and Hydrogen," Journal of Catalysis, vol. 145, pp. 344-355, (1994).

Zhao, Guanhong et al., "Catalytic Conversion of Cellulose to Ethylene Glycol over Tungsten Phosphide Catalysts," Chinese Journal of Catalysis, vol. 31, No. 8, pp. 928-932, (2010).

Clark, Paul et al., "Synthesis and Activity of a New Catalyst for Hydroprocessing: Tungsten Phosphide," Journal of Catalysis, vol. 200, pp. 140-147, (2001).

Clark, Paul et al., "Characterization of Silica-Supported Molybdenum and Tungsten Phosphide Hydroprocessing Catalysts by 31P Nuclear Magnetic Resonance Spectroscopy," Journal of Catalysis, vol. 207, pp. 256-265, (2002).

Apr. 3, 2014 Search Report issued in International Patent Application No. PCT/CN2013/090604.

Sep. 9, 2016 Search Report issued in European Patent Application No. 13870898.7.

Patil, Pratap T. et al., "Heterogeneously Catalyzed Hydroprocessing of Organosolv Lignin in Sub- and Supercritical Solvents," Energy Fuels, vol. 25, pp. 4713-4722 (2011).

Zakzeski, Joseph et al., "The Catalytic Valorization of Lignin for the Production of Renewable Chemicals," Chemical Reviews, vol. 110, pp. 3552-3599 (2010).

Romero, Y. et al., "Hydrodeoxygenation of benzofuran and its oxygenated derivatives (2,3-dihydrobenzofuran and 2-ethylphenol) over NiMoP/Al2O3 catalyst," Applied Catalysis A: General, vol. 353, pp. 46-53 (2009).

Jun. 1, 2015 Office Action issued in Chinese Patent Application No. 2013102011650.

Jun. 3, 2015 Office Action issued in Chinese Patent Application No. 201310201271.9.

Feb. 4, 2016 Office Action issued in Chinese Patent Application No. 201310008112.7.

Sep. 26, 2016 Office Action issued in Chinese Patent Application No. 201310008112.7.

* cited by examiner

USE OF CATALYST PREPARED WITH A SUBGROUP VI ELEMENT FOR THE PRODUCTION OF ORGANIC CHEMICALS AND FUELS FROM LIGNIN

TECHNICAL FIELD

This invention refers to a method through which biomass was converted into liquid fuels and organic chemicals. More specifically, it is a process in which lignin polymer is broken down into molecules with molecular weight 16-3000 including hydrocarbons, alcohols, esters, benzyl alcohols, phenols, aromatic monomers and oligomers.

BACKGROUND

Nowadays, due to the increasing depletion of fossil fuels, exploring the clean renewable energy resources has become an urgent issue. Biomass, including cellulose, hemicellulose, and lignin, is one of the most widely renewable resources in the world. Cellulose and hemicellulose have been widely used, while lignin which accounts for 25% of the lignocellulosic biomass, is still not commonly used, which causes waste of resources and pollution of the environment. There has been many researches performed on the conversion of lignin, which includes pyrolysis, base hydrolysis, supercritical water hydrolysis etc. However, these methods mentioned above need harsh reaction conditions and always give low product yields. Therefore, the development of a fast, effective and environmentally friendly method of lignin depolymerization has attracted the attention of researchers. Lignin is a three dimensional amorphous polymer in which methoxylated phenylpropanes are connected with ether and carbon-carbon bonds. Lignin, as a primary component of plant biomass, contains many oxygen functional groups (hydroxyl, carboxyl, carbonyl groups, ether and ester bonds). Therefore, phenolic chemicals can be obtained from lignin by a chemical degradation processes. There are two major challenges for the application of lignin as a source of chemicals and materials. Firstly, the polyphenolic structure is chemically very stable, and therefore, difficult to transform or structurally modify. Moreover, it contains a large amount of functional groups which facilitate the condensation reactions during the depolymerization.

CONTENTS OF THE INVENTION

The aim of the present invention is to overcome the shortcomings of existing technology and provides a process through which lignin can be catalytically converted into high valued molecules with the synergistic action of reactive solvents and catalysts. The goal of this technological invention is achieved through the following technical scheme:

The described catalysts made of the Group VIB elements such as molybdenum or tungsten. The described molybdenum based catalyst can be a supported or an unsupported catalyst. The metal loading amount of the supported catalyst is between 1-80 wt. %, with a preferred range of 5-30 wt. %. The described supported catalysts are as follows: $A_xB_y/C$ supported catalyst, among which A represents molybdenum, B represents carbon, phosphorus, oxygen or nitrogen element, C is the support of the catalyst including aluminum oxide ($Al_2O_3$), activated carbon (AC), silicon dioxide ($SiO_2$), silicon carbide (SiC), zeolites or carbon fiber and other common supports. The support increases the surface area and supply suitable pore structure, which is needed in order to increase the stability and activity of the catalyst, $0<x\leq2$, $0<y\leq3$, a preferred range is $1\leq x\leq2$, that is molybdenum metal, molybdenum carbides, molybdenum phosphide, molybdenum nitride, molybdenum oxide with different valences are used as the active center which is supported on the support. The described unsupported catalysts are shown as follows: $A_xB_y$ unsupported catalyst, among which A represents the molybdenum, B represents carbon, phosphorus, oxygen or nitrogen element, $0<x\leq2$, $0<y\leq3$, a preferred range is $1\leq x\leq2$, that is molybdenum metal, molybdenum carbides, molybdenum phosphide, molybdenum nitride, molybdenum oxide with different valences are used directly as catalyst.

The molybdenum-based catalyst mentioned above can also been used with a promoter Z. The loading of Z, which is the mass ratio of metal Z and the total mass of catalyst, is between 0.1-15%, with a preferred range of 0.1-10 wt. %. The promoter Z is one of the following metals, Fe, Ni, Co, Ru, W, Cu, Cr, Pt, and their compounds. The promoted molybdenum-based catalyst can be shown as Z-AB/C supported catalyst, among which Z is the promoter, A is the molybdenum, B is carbon, phosphorus, oxygen or nitrogen and C is the support.

The molybdenum-based catalyst mentioned above is synthesized by temperature programmed reduction after incipient-wetness impregnation. Specifically, the procedure for synthesis of a supported molybdenum carbide catalyst is shown as follows: (1) The support was impregnated with an aqueous solution containing molybdenum and then the material was dried at 80-150° C. (2) The carbide catalyst can be obtained from the temperature programmed carbonization of the dried materials (P. P. Aegerter et al, Journal of Catalysis, 1996, 164, 109-121). The procedure for synthesis of a supported molybdenum phosphide catalyst is shown as follows: The support was impregnated with an aqueous solution containing molybdenum and ammonium phosphate, then the material was dried at 80-150° C. The phosphide catalyst can be obtained from the temperature programmed reaction of the dried materials. The procedure for the synthesis of a supported molybdenum nitride catalyst is shown as follows: The support was incipient-wetness impregnated with an aqueous solution containing molybdenum, then the material was dried at 80-150° C. The nitride catalyst can be obtained from the temperature programmed nitridation of the dried materials (S. Korlann, Chemistry of Materials, 2002, 14, 4049-4058). The $MoO_3$ catalyst can be obtained after being calcined at 500° C. for 4 h in nitrogen. The $MoO_2$ catalyst can be obtained after being calcined at 350° C. for 12 h in hydrogen. The Mo catalyst can be obtained after reduction of the $MoO_3$ catalyst at 650° C. for 4 h in hydrogen. The unsupported molybdenum based catalyst mentioned above can be prepared by temperature programmed reaction. Specifically, the unsupported molybdenum carbide catalyst can be obtained from the temperature program carbonization of the molybdenum salt (T. Miyao et al., Applied Catalysis A: General, 1997, 165, 419-428; J. S. Lee et al., Journal of Catalysis, 1990, 125, 157-170; C. H. Liang et al., Chemistry Materials, 2002, 14, 3148-3151). The unsupported molybdenum phosphide catalyst can be obtained from the temperature programmed reaction of the mixture of molybdenum salt and ammonium phosphate (C. Stinner et al., Journal of Catalysis, 2000, 191, 438-444). The unsupported molybdenum nitride catalyst can be obtained from the temperature programmed nitridation of the molybdenum salt (R. S. Wise et al., Journal of Catalysis, 1994, 145, 344-355). The unsupported $MoO_3$ catalyst can be obtained from the molybdenum salt after being calcined at 500° C. for 4 h in nitrogen. The unsupported $MoO_2$ catalyst can be obtained the molybdenum salt after being calcined at 350° C. for 12 h in hydrogen. The unsupported molybdenum catalyst can be obtained from the molybdenum salt after reduction at 650° C. for 4 h in hydrogen.

Transition metal tungsten was selected to be the active metal in the W-based catalysts, wherein the catalysts were unsupported or supported. The supported ones were denoted as AB/C, where A indicates the metal tungsten, B indicates the phosphorus element, and C denotes the catalyst support, including $Al_2O_3$, AC, $SiO_2$, SiC, zeolites, carbon nanofibres, or other commons materials used as the catalyst supports. The support was used to increase the effective surface area and provide the suitable porous structure of the catalyst, to improve the stability of the catalyst and increase the amount of the active sites. In the catalyst, the content of the active W compound was 1-50 wt. %, with a preferred range of 5-30 wt. % The unsupported catalyst was WP. In the above catalyst, promoter Z was also used to modify the catalyst. The content of Z was defined as the mass of Z divided by the entire mass of the catalyst including the promoter, phosphide and support. The promoter used includes one of the following elements, Fe, Ni, Co, Ru, Cu, Cr, Pt, and their compounds, wherein the content was 0.1-15%, with a preferred content of 0.1-10%. The promoter was used to improve the electron state of the catalyst, so as to improve the catalytic performance, and to obtain better activity of the lignin. Take the supported catalyst as a sample, i.e. Z-AB/C, Z means the promoter, A means the transition metal W, B means the phosphorus element, and C means the support. The supported W-based catalyst was obtained by the impregnation method followed by temperature programmed reaction. The solution of the salt of the active component and diammonium hydrogen phosphate was used to impregnate the support, after drying and calcination at 500° C., the catalyst precursor was reduced under flowing hydrogen atmosphere with temperature programmed heating. The supported phosphide catalyst with promoter was prepared through the following method, using Ni-WP/AC as the sample: place a specified amount of the diammonium hydrogen phosphate, nickel nitrate and ammonium meta-tungstate into water, after dissolving, use the solution to impregnate the AC support, then dry the material at 120° C. for 12 h, and finally reduce the material under the flowing hydrogen atmosphere (G. H. Zhao et al., Chinese Journal of Catalysis 2010, 31, 928-932). The unsupported WP catalyst was also prepared under the flowing hydrogen atmosphere (P. Clark et al., Journal of Catalysis, 2001, 200, 140-147). The supported WP catalyst was also prepared through the impregnation method and then reduction in hydrogen atmosphere (P. Clark et al., Journal of Catalysis, 2002, 207, 256-265).

In addition to the supported and unsupported Mo-based and W-based catalysts prepared by incipient wetness impregnation and temperature programmed reduction, we prepared amorphous alloy catalysts with the same composition mentioned above, that is, the same active metal species, promoters, supports and their amounts are the same as those used in the above-mentioned catalysts. The precursors are reduced with reducants to get the amorphous alloy catalysts. In the supported catalysts, active metals accounts for 1-80 wt. % of the catalyst, optimized to 5-30 wt. %. Promoters accounts for 0.1-15 wt. % of the catalysts, optimized to 0.1-10 wt. %. In unsupported catalysts, the promoters accounts for 0.1-15 wt. % of the catalysts, optimized to 0.1-10 wt. %.

(1) The preparation of the supported Mo—B amorphous alloy: The support was impregnated with an aqueous solution containing molybdenum. Then the material was dried at 80-200° C. to get the catalyst precursor. The precursor was reduced by $NaBH_4$ or $KBH_4$ under stirring in an ice-water bath. When the reaction was completed, the catalyst was filtrated and washed to pH=7 and then washed with organic solvent. The as prepared catalyst was denoted as supported Mo—B amorphous alloy.

(2) The preparation of the supported Mo—P amorphous alloy: The support was impregnated with an aqueous solution containing molybdenum. Then the material was dried at 80-200° C. to get the catalyst precursor. The precursor was reduced by sodium hypophosphite under stirring in an ice-water bath. When the reaction was completed, the catalyst was filtrated and washed to pH=7 and then washed with organic solvent. The as prepared catalyst was denoted as supported Mo—P amorphous alloy.

(3) The preparation of doped supported Mo—B—X amorphous alloy: The support was impregnated with an aqueous solution containing molybdenum and salts of promoting metal X (X=Fe, Ni, Co, W, Ru, Cu, Cr or Pt). Then the material was dried at 80-200° C. to get the catalyst precursor. The precursor was reduced by $NaBH_4$ or $KBH_4$ under stirring in an ice-water bath. When the reaction was completed, the catalyst was filtrated and washed to pH=7 and then washed with organic solvent. The as prepared catalyst was denoted as supported Mo—B—X amorphous alloy.

(4) The preparation of doped supported Mo—P—X amorphous alloy: The support was impregnated with an aqueous solution containing molybdenum and salts of promoting metal X (X=Fe, Ni, Co, W, Ru, Cu, Cr or Pt). Then the material was dried at 80-200° C. to get the catalyst precursor. The precursor was reduced by sodium hypophosphite under stirring in an ice-water bath. When the reaction was completed, the catalyst was filtrated and washed to pH=7 and then washed with organic solvent. The as prepared catalyst was denoted as supported Mo—P—X amorphous alloy.

(5) The preparation of unsupported Mo—B amorphous alloy: molybdenum salts were dissolved in aqueous ammonia and then the solution was added into aqueous $NaBH_4$ under stirring. When the reaction was completed, the material was filtrated and washed with water. The as prepared catalyst was denoted as Mo—B amorphous alloy.

(6) The preparation of unsupported Mo—P amorphous alloy: molybdenum salts were dissolved in aqueous ammonia and then the solution was added into aqueous sodium hypophosphite under stirring. When the reaction was completed, the material was filtrated and washed with water. The as prepared catalyst was denoted by Mo—P amorphous alloy.

(7) The preparation of doped unsupported Mo—B amorphous alloy: molybdenum salts and salts of doping metal X (X=Fe, Ni, Co, W, Ru, Cu, Cr or Pt) were dissolved in aqueous ammonia and then the solution was added into aqueous $NaBH_4$ under stirring. When the reaction was completed, the material was filtrated and washed with water. The as prepared catalyst was denoted as Mo—B—X amorphous alloy.

(8) The preparation of doped unsupported Mo—P amorphous alloy: molybdenum salts and salts of doping metal X (X=Fe, Ni, Co, W, Ru, Cu, Cr or Pt) were dissolved in aqueous ammonia and then the solution was added into aqueous sodium hypophosphite solution under stirring. When the reaction was completed, the material was filtrated and washed with water. The as prepared catalyst was denoted as Mo—P—X amorphous alloy.

The molybdenum or tungsten based catalyst mentioned above was used in the catalytic depolymerization of lignin into organic chemicals. For a typical run, the lignin, catalyst and solvent were loaded into the reactor. The reactor was sealed and pressurized to the desired value. The reactor was then heated to 230° C.-350° C. and remained for 0.5 h-12 h. After the reaction, the reaction mixture was filtrated and rotary vacuum evaporated. Finally the liquid product was obtained. In the process mentioned above, the lignin employed contained Kraft lignin, enzymatic hydrolysis lignin, Klason lignin, Milled wood lignin and organosolv lignin. The sealed reactor was evacuated and purged with inert gas (such as nitrogen, argon and helium) or hydrogen. The solvent employed is water, ethanol or a mixture of water and ethanol with any proportion, for example the volume faction of ethanol is between 10% and 50%. Continuous feed reactor for both liquid and solid or slurry and continuous distillation were used in the process to maintain the continuous process. The mass ratio of the lignin and solvent is between 1:200 and 1:10, with a preferred range of 1:100-1:80. The mass ratio of the lignin and catalyst is between 1:1 and 200:1, and a preferred range is 10:1-100:1. The initial reaction pressure is 0-6 MPa at room temperature, the stirring rate is 100-1500 r/min, the reaction temperature is in 260-300° C., and the reaction time is 2-6 h.

Figure 1:
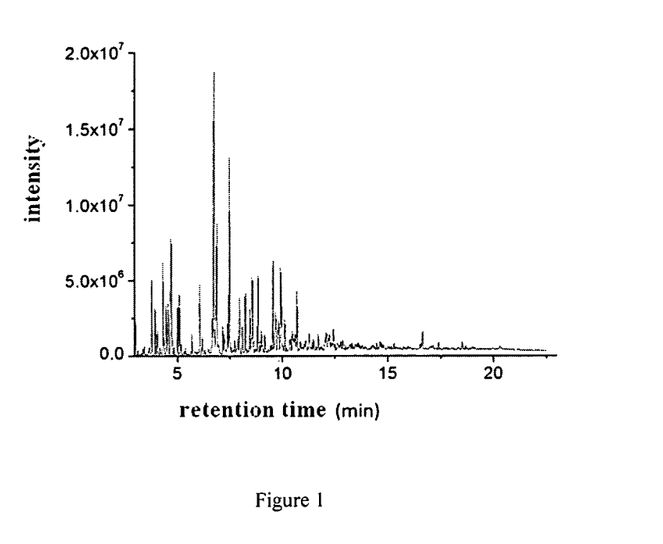
FIG. 1: Total ionic chromatogram of the liquid products obtained from the lignin depolymerization reaction at 280° C. for 6 h in pure ethanol over $Mo_2C/AC$. (1)
Figure 2:
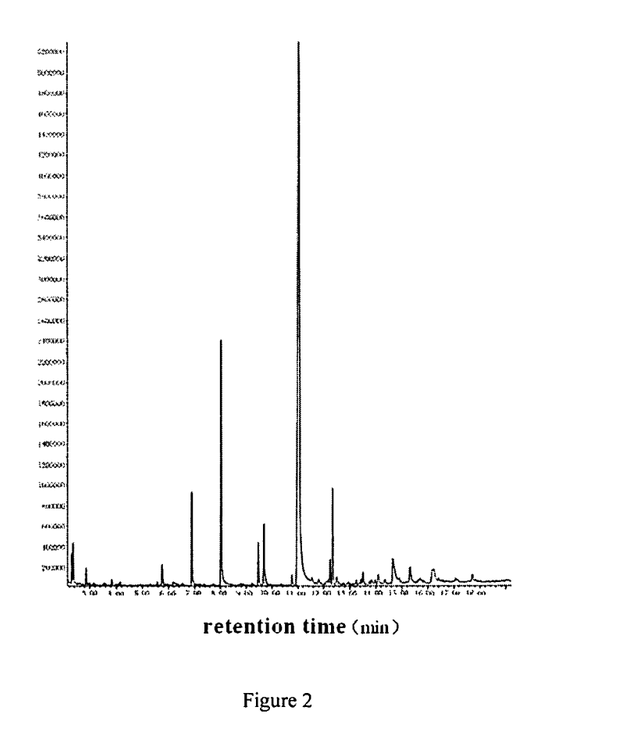
FIG. 2: Total ionic chromatogram of the liquid products obtained from the lignin depolymerization reaction at 280° C. for 6 h in water/ethanol (v:v=1:1) over $W_2P/AC$. (2)

The liquid product obtained from the depolymerization of lignin was analyzed with gas chromatography, high performance liquid chromatography and gel permeation chromatography. The typical total ion chromatogram was shown as FIG. 1 and FIG. 2. The liquid product contains alcohols (monohydric alcohols such as butanol, butenol, hexyl alcohol, 2-hexenol, 2-ethyl butanol, 2-methyl pentenol, and polyhydric alcohols with a hydroxyl value from 100 to 1000 mg KOH/g), esters (ethyl acetate, butyl acetate, ethyl butyrate, ethyl hexanoate, ethyl 3-hexenoate, ethyl 2-hexenoate, ethyl 3-methylpentanoate, ethyl 4-octanoate, ethyl octanoate), phenols (guaiacol, 4-methyl guaiacol, 4-ethyl guaiacol, 4-propyl guaiacol), benzyl alcohols (benzyl alcohol, 2-methyl benzyl alcohol, 4-ethyl benzyl alcohol, 2,4,5-trimethyl benzyl alcohol) and arenes (toluene, xylene, 3-methyl ethylbenzene, 2,4-dimethyl ethylbenzene, 2,5-dimethyl ethylbenzene). The total liquid products are shown as follows:

| Type | Retention time (min) | Molecular formula | Name |
|---|---|---|---|
| Alcohols | 2.52 | $C_4H_{10}O$ | butanol |
|  | 2.54 | $C_4H_8O$ | butenol |
|  | 4.32 | $C_6H_{14}O$ | 2-ethyl butanol |
|  | 4.47 | $C_6H_{12}O$ | 2-hexenol |
|  | 4.57 | $C_6H_{12}O$ | 2-methyl pentenol |
|  | 4.72 | $C_6H_{14}O$ | hexyl alcohol |
| Esters | 2.21 | $C_4H_8O_2$ | ethyl acetate |
|  | 3.72 | $C_6H_{12}O_2$ | ethyl butyrate |
|  | 3.87 | $C_6H_{12}O_2$ | butyl acetate |
|  | 6.64 | $C_8H_{14}O_2$ | ethyl 3-methylpentanoate |
|  | 6.71 | $C_8H_{16}O_2$ | ethyl hexanoate |
|  | 6.81 | $C_8H_{14}O_2$ | ethyl 3-hexenoate |
|  | 7.48 | $C_8H_{14}O_2$ | ethyl 2-hexenoate |
|  | 9.47 | $C_{10}H_{16}O_2$ | ethyl 4-octanoate |
|  | 9.68 | $C_{10}H_{16}O_2$ | ethyl 3-octanoate |
|  | 9.78 | $C_{10}H_{16}O_2$ | ethyl 2-octanoate |
|  | 9.92 | $C_{10}H_{18}O_2$ | ethyl octanoate |
| Phenols | 8.27 | $C_7H_8O_2$ | guaiacol |
|  | 9.47 | $C_8H_{10}O_2$ | 3-methyl guaiacol |
|  | 9.95 | $C_8H_{10}O_2$ | 4-methyl guaiacol |
|  | 12.27 | $C_9H_{12}O_2$ | 4-ethyl guaiacol |
|  | 12.23 | $C_9H_{10}O_3$ | 4-acetyl guaiacol |
|  | 12.61 | $C_{10}H_{14}O_2$ | 4-propyl guaiacol |
| Benzyl alcohols | 7.36 | $C_7H_8O$ | Benzyl alcohol |
|  | 9.15 | $C_8H_{10}O$ | Methyl benzyl alcohol |
|  | 10.47 | $C_9H_{12}O$ | Ethyl benzyl alcohol |
|  | 13.06 | $C_{10}H_{14}O$ | Trimethyl benzyl alcohol |
| Arenes | 3.43 | $C_7H_8$ | Methylbenzene |
|  | 5.11 | $C_8H_{10}$ | xylene |
|  | 6.18 | $C_9H_{12}$ | Methyl ethylbenzene |
|  | 7.25 | $C_9H_{10}$ | alkyl benzene |
|  | 8.23 | $C_{10}H_{14}$ | Dimethyl ethylbenzene |

Compared with the existing technology, this process is advantageous in many aspects. (1) Lignin is an abundant biomass in nature with wide resources and low-cost. (2) The lignin from black liquor in the pulping process and cellulosic ethanol industry can be used as the feedstock. (3) Water or ethanol is employed as the reactive solvent, which are environmentally benign and non-pollutive. (4) Aromatic parts of the lignin molecule were transferred to the aromatic compounds while alcohols and esters were obtained from the side chains of the lignin. (5) A high yield of liquid products, without formation of tar and char, is obtained in the lignin depolymerization. The overall yield of small molecules is in excess of 100 wt. % under optimum conditions. This is because that the solvent is a reactant and gives rise to ethyl esters and other value added products.

IMPLEMENTING CASES

The First Group of Examples: Depolymerization of Lignin with Molybdenum Based Catalyst The invention will be further introduced with the following examples. Ammonium paramolybdate was used as the source of molybdenum. Ammonia water was purchased from Guangfu Inc.

Example 1-1

For a typical preparation, activated carbon (AC) was impregnated with the solution of ammonium molybdate with extra ammonia, then the material was dried at 120° C. for 12 h. The precursor was finally carburized using a temperature programmed reaction procedure. Specifically, 0.5 g sample was exposed to hydrogen, and heated to 350° C. and held at this temperature for 12 h. The gas was then switched to 15% $CH_4/H_2$, and the temperature was increased to 590° C. and then held at the temperature for 2 h. The sample was then cooled to room temperature (25° C.). The catalyst was represented as $Mo_2C/AC$ (30 wt. % $Mo_2C/AC$).

Example 1-2

With the exception of the Mo content, the same catalyst synthesis process was used as in example 1-1. The content of Mo in the $Mo_2C/AC$ catalyst was set as 1 wt. %, 5 wt. %, 10 wt. %, 15 wt. %, 20 wt. %, 30 wt. %, 50 wt. % and 80 wt. % with changing the concentration of ammonium molybdate or with repeated impregnation.

Example 1-3

The same catalyst synthesis process was used as in example 1-1, except that the catalyst support was changed from AC to alumina ($Al_2O_3$), silicon carbide (SiC), silicon dioxide ($SiO_2$). Therefore, molybdenum carbide catalysts with different support were obtained. For example: $Mo_2C/Al_2O_3$, $Mo_2C/SiO_2$, $Mo_2C/SiC$.

Example 1-4

The same process of catalyst synthesis was used as in example 1-1, except that the final carbonization temperature was changed to 560° C., 620° C., 650° C., 680° C., 710° C., and 740° C. As a consequence, $Mo_xC_y/AC$ samples with different crystal form are obtained, where $0<x\leq 2$, $0\leq y\leq 1$, x is 1, 1, 2, 1, 2, 2; y is 1, 0, 0.5, 0.8, 0.2, 0.6.

Example 1-5

The same process of catalyst synthesis was employed as in example 1-1, except that the sample was exposed to nitrogen, and heated to 500° C. and held at this temperature for 4 h. The catalyst was represented as $MoO_3/AC$.

Example 1-6

The same process of catalyst synthesis was employed as in example 1-1, except that the sample was exposed to hydrogen, and heated to 350° C. and held at this temperature for 12 h. The $CH_4/H_2$ was not needed in the preparation of this example. The catalyst was represented as $MoO_2/AC$.

Example 1-7

The same process of catalyst synthesis was employed as in example 1-1, except that the sample was exposed to hydrogen, and heated to 650° C. and held at this temperature for 4 h. The catalyst was represented as Mo/AC.

Example 1-8

AC was impregnated with a solution of diammonium hydrogen phosphate and ammonium molybdate, then the mixtures were dried at 120° C. for 12 h and calcined at 500° C. for 4 h. The precursor was exposed to hydrogen, and heated to 650° C. and held at this temperature for 2 h. The catalyst was represented as MoP/AC.

Example 1-9

The prepared catalysts were transferred into the batch reactor which was loaded with 1.0 g Kraft lignin (purchased from Sigma-Aldrich), 0.5 g catalyst and 100 mL ethanol. The initial gas pressure was 2 MPa of hydrogen. After reaction for 2 h at set 280° C., the system was cooled to room temperature. After releasing the gas, the reaction mixture was filtrated and analyzed. The liquid products were qualitatively analyzed with GC-MS (Agilent GC6890-MS5973), and quantitatively analyzed with GC (Agilent GC6890 with a FID) with internal standard method. The columns used with the FID and MS detector were both HP-5MS capillary columns (30 m×0.25 mm×0.25 μm). The yield of liquid products was expressed as mg/g lignin. The liquid product contains alcohols (monohydric alcohols such as butanol, butenol, hexyl alcohol, 2-hexenol, 2-ethyl butanol, 2-methyl pentenol), esters (ethyl acetate, butyl acetate, ethyl butyrate, ethyl hexanoate, ethyl 3-hexenoate, ethyl 2-hexenoate, ethyl 3-methylpentanoate, ethyl 4-octanoate, ethyl octanoate), phenols (guaiacol, 4-methyl guaiacol, 4-ethyl guaiacol, 4-propyl guaiacol), benzyl alcohols (benzyl alcohol, 2-methyl benzyl alcohol, 4-ethyl benzyl alcohol, 2,4,5-trimethyl benzyl alcohol) and arenes (toluene, xylene, 3-methyl ethylbenzene, 2,4-dimethyl ethylbenzene, 2,5-dimethyl ethylbenzene).

Example 1-10

The yields (mg/g lignin) of grouped compounds obtained with different Mo-based catalysts ($Mo_2C/AC$, Mo/AC, $MoO_2/AC$, $MoO_3/AC$) are listed as follows. The reaction conditions were the same as in Example 1-9. High yield of liquid products were obtained from Mo-based catalysts, among which $Mo_2C/AC$ showed the highest activity.

| Catalyst | Yield of alcohols | Yield of esters | Yield of phenols | Yield of benzyl alcohols | Yield of arenes |
| --- | --- | --- | --- | --- | --- |
| $Mo_2C/AC$ | 139 | 215 | 44 | 34 | 14 |
| MoP/AC | 54 | 122 | 32 | 33 | 7 |
| Mo/AC | 44 | 126 | 26 | 31 | 5 |
| $MoO_2/AC$ | 12 | 85 | 21 | 20 | 5 |
| $MoO_3/AC$ | 14 | 63 | 21 | 10 | 4 |
| No catalyst | 5 | 31 | 18 | none | none |

Example 1-11

The effect of the supports ($Mo_2C/AC$, $Mo_2C/Al_2O_3$, $Mo_2C/SiO_2$, $Mo_2C/SiC$, $Mo_2C$) on the yields (mg/g lignin) of the grouped compounds are shown as follows. The reaction conditions were the same as in Example 1-9. High yield of liquid products were obtained from Mo-based catalysts with different supports, among which $Mo_2C/AC$ shows the highest activity.

| Catalyst | Yield of alcohols | Yield of esters | Yield of phenols | Yield of benzyl alcohols | Yield of arenes |
| --- | --- | --- | --- | --- | --- |
| $Mo_2C/AC$ | 133 | 215 | 44 | 34 | 14 |
| $Mo_2C/Al_2O_3$ | 112 | 162 | 43 | 22 | 8 |
| $Mo_2C/SiO_2$ | 103 | 186 | 41 | 32 | 9 |
| $Mo_2C/SiC$ | 99 | 174 | 46 | 27 | 9 |
| $Mo_2C$ | 86 | 133 | 40 | 23 | 8 |

Example 1-12

The effect of Mo loading (30 wt. % $Mo_2C/AC$, 20 wt. % $Mo_2C/AC$, 10 wt. % $Mo_2C/AC$) on the yields (mg/g lignin) of the grouped compounds are shown as follows. The reaction conditions were the same as in Example 1-9. High yields of liquid products were obtained from Mo-based catalysts with different Mo loading, among which 30 wt. % $Mo_2C/AC$ showed the highest activity.

| Catalyst | Yield of alcohols | Yield of esters | Yield of phenols | Yield of benzyl alcohols | Yield of arenes |
|---|---|---|---|---|---|
| 30 wt. % | 133 | 215 | 44 | 34 | 14 |
| 20 wt. % | 132 | 204 | 31 | 35 | 17 |
| 10 wt. % | 82 | 163 | 32 | 35 | 12 |
| 5 wt. % | 82 | 139 | 32 | 38 | 12 |

Example 1-13

The effect of different carbonization temperature on the yields (mg/g lignin) of the grouped products are shown as follows. The reaction conditions were the same as in Example 1-9. High yields of liquid products were obtained with Mo-based catalysts with different carbonization temperatures, among which the highest yield of liquid was obtained at 590° C.

| Carbonization temperature (° C.) | Yield of alcohols | Yield of esters | Yield of phenols | Yield of benzyl alcohols | Yield of arenes |
|---|---|---|---|---|---|
| 560 | 84 | 71 | 40 | 11 | 10 |
| 590 | 133 | 215 | 44 | 34 | 14 |
| 650 | 96 | 143 | 42 | 27 | 11 |
| 710 | 67 | 165 | 42 | 14 | 10 |

Example 1-14

The effect of solvent on the yields (mg/g lignin) of the grouped products are shown as follows. The reaction conditions were the same as in Example 1-9, with the exception of the solvent used. Only phenols were obtained in the water solvent and the highest overall yield of liquid product was obtained with ethanol as the solvent.

| Solvent | Yield of alcohols | Yield of esters | Yield of phenols | Yield of benzyl alcohols | Yield of arenes |
|---|---|---|---|---|---|
| Water | no | no | 49 | no | No |
| Water/ethanol | 21 | 37 | 44 | no | no |
| Ethanol | 133 | 215 | 44 | 34 | 14 |

Example 1-15

The effect of the initial hydrogen pressure on the yields (mg/g lignin) of the grouped products are shown as follows. The reaction conditions were the same as in Example 1-9, with the exception of the initial hydrogen pressure.

| Initial hydrogen pressure (MPa) | Yield of alcohols | Yield of esters | Yield of phenols | Yield of benzyl alcohols | Yield of arenes |
|---|---|---|---|---|---|
| 0 | 63 | 251 | 40 | 39 | 22 |
| 1 | 119 | 213 | 49 | 39 | 17 |
| 2 | 133 | 215 | 44 | 34 | 14 |
| 3 | 110 | 165 | 23 | 49 | 16 |
| 4 | 87 | 95 | 24 | 31 | 11 |
| 5 | 74 | 93 | 23 | 31 | 10 |
| 6 | 69 | 84 | 22 | 30 | 8 |

Example 1-16

The effect of the reaction time on the yields (mg/g lignin) of the grouped products are shown as follows. The reaction conditions were the same as in Example 1-9, with the exception of the reaction time.

| Reaction time (h) | Yield of alcohols | Yield of esters | Yield of phenols | Yield of benzyl alcohols | Yield of arenes |
|---|---|---|---|---|---|
| 0.5 | 2 | 5 | 12 | 2 | 1 |
| 2 | 133 | 215 | 44 | 34 | 14 |
| 4 | 178 | 189 | 23 | 49 | 43 |
| 6 | 155 | 134 | 19 | 57 | 39 |
| 12 | 164 | 128 | 16 | 35 | 39 |

Example 1-17

The effect of the gas atmosphere on the yields (mg/g lignin) of the products are shown as follows. The reaction conditions were the same as in Example 1-9, with the exception of the gas atmosphere.

| Gas atmosphere | Yield of alcohols | Yield of esters | Yield of phenols | Yield of benzyl alcohols | Yield of arenes |
|---|---|---|---|---|---|
| $H_2$-0 MPa | 63 | 251 | 40 | 39 | 22 |
| $N_2$-0 MPa | 57 | 262 | 43 | 42 | 23 |

Example 1-18

The effect of the reaction time on the yields (mg/g lignin) of the grouped products under nitrogen atmosphere are shown as follows. The reaction conditions were the same as in Example 1-9, with the exception of the reaction time.

| Reaction time (h) | Yield of alcohols | Yield of esters | Yield of phenols | Yield of benzyl alcohols | Yield of arenes |
|---|---|---|---|---|---|
| 0.5 | 13 | 29 | 3 | 3 | 1 |
| 2 | 57 | 283 | 43 | 42 | 23 |
| 4 | 139 | 469 | 50 | 91 | 56 |
| 6 | 252 | 368 | 57 | 123 | 113 |
| 12 | 278 | 406 | 78 | 71 | 131 |

Example 1-19

The prepared catalysts were transferred to the batch reactor which was loaded with 1.0 g enzymatic hydrolysis lignin, 0.5 g catalyst and 100 mL ethanol. The initial gas pressure was 0 MPa of nitrogen. After reaction for 6 h at 280° C., the system was cooled to room temperature. After releasing the gas, the reaction mixture was filtrated and analyzed. The liquid product contained alcohols (polyhydric alcohols), phenols (guaiacol, 4-methyl guaiacol, 4-ethyl guaiacol, 4-propyl guaiacol, 4-propenyl guaiacol, 2-ethyl phenol, 4-ethyl phenol, 2,5-diethyl phenol), benzyl alcohols (benzyl alcohol, 2-methyl benzyl alcohol). The hydroxyl number of liquid products were analyzed according to the methods of ISO 14900:2001, Plastics—polyols for use in the production of polyurethane—Determination of hydroxyl number. The weight-average molecular weight ($M_w$) and Polydispersity index (PDI) of liquid products were measured with a GPC-HPLC instrument, UV detector set at 270 nm, Waters Styragel HR1 column at 40° C.) using tetrahydrofuran as the eluent at a flow rate of 1 ml/min with linear polystyrene standards for the molecular weight calibration curve. Phenols and benzyl alchols were qualitatively analyzed with GC-MS (Agilent GC6890-MS5973). The columns used with the FID and MS detector were both HP-5MS capillary columns (30 m×0.25 mm x 0.25 μm). The yield of liquid products was expressed as mg/g lignin.

The effect of the reaction temperature on the yield (mg/g lignin) of liquid products, hydroxyl number, $M_w$ and PDI of liquid products obtained from the lignin depolymerization are shown as follows. The reaction conditions were the same as in Example 19, with the exception of the reaction temperature.

| Reaction temperature (° C.) | Yield of liquid products | Hydroxyl number (mg KOH/g) | $M_w$ | PDI |
|---|---|---|---|---|
| 240 | 689 | 236 | 2480 | 2.58 |
| 260 | 783 | 289 | 2246 | 2.36 |
| 280 | 936 | 345 | 1860 | 2.12 |
| 300 | 994 | 289 | 1099 | 1.83 |
| 320 | 995 | 268 | 1065 | 2.23 |

Example 1-20

The effect of reaction time on the yield (mg/g lignin) of liquid products, hydroxyl number, $M_w$ and PDI of the liquid products obtained from the lignin conversion are shown as follows. The reaction conditions were the same as in Example 1-19, with the exception of the reaction time.

| Reaction time (h) | Yield of liquid products | Hydroxyl number (mg KOH/g) | $M_w$ | PDI |
|---|---|---|---|---|
| 2 | 835 | 326 | 1820 | 2.28 |
| 3 | 994 | 289 | 1099 | 1.83 |
| 4 | 962 | 332 | 1230 | 2.13 |
| 5 | 983 | 310 | 1450 | 2.09 |
| 6 | 992 | 298 | 1580 | 2.15 |

In the examples mentioned above, Klason lignin, milled wood lignin, organosolv lignin, enzymatic hydrolysis lignin can be used as the feedstock to produce aliphatic hydrocarbons, alcohols, esters, phenols, benzyl alcohols, polyols and arenes. The mass ratio of the lignin and solvent is 1:200-1:10, and a preferred range is 1:100-1:80. The mass ratio of the lignin and catalyst is 1:1-200:1, and a preferred range is 10:1-100:1. The reaction temperature is 250-350° C., and a preferred range is 260-300° C. The stirring rate is 100-1500 r/min.

The Second Group of Examples: Decomposition of Lignin with Molybdenum Nitride Catalyst Example 2-1

For a typical preparation, alumina was impregnated with the solution of ammonium heptamolybdate and the material was dried at 110° C. for 12 h. The samples were then nitrided with a $N_2$, $H_2$ (v: v=1:5) mixture following under a four-stage heating ramp: from RT to 350° C. at 10° C./min, and then to 500° C. at 1° C./min and then to 700° C. at 2° C./min, maintaining at that temperature for 2 h. Then the catalyst with an Mo content of 30% was obtained and marked $Mo_2N/\gamma$-$Al_2O_3$ (S. Korlann, Chemistry of Materials, 2002, 14, 4049-4058).

Example 2-2

The same process of catalyst synthesis was used as in example 2-1. Mo2N/γ-Al2O3 Catalysts with different Mo contents (10%, 20%, 30%, 46 wt. %) were synthesized with changing the concentration of the ammonium heptamolybdate solution s or stepwise impregnation.

Example 2-3

The same process of catalyst synthesis was employed as in example 2-1, except that the catalyst support was changed from alumina to NaY zeolite (NaY), $SiO_2$ to obtain $Mo_2N$/NaY and $Mo_2N/SiO_2$.

Example 2-4

The same process of catalyst synthesis was employed as in example 2-1, except that the final nitration temperatures were changed to 600° C., 650° C., 700° C. and 750° C.

Example 2-5

The Kraft lignin was dried overnight at 373 K for 12 h before being used. The prepared catalyst was transferred to the batch reactor which was loaded with 1.00 g Kraft lignin and 100 ml ethanol with nitrogen as shielding gas. After reaction for 6 h at a set temperature, the system was cooled to room temperature. After releasing the gas, the reaction mixture was filtrated and rotary evaporated. The liquid products were qualitatively analyzed with GC-MS (Agilent GC6890-MS5973), and quantitatively analyzed with GC (Agilent GC6890 with a FID) with internal tagging method. The columns used with the FID and MS detector were both HP-5MS capillary columns (30 m×0.25 mm×0.25 μm). The yield of liquid products was calculated as: (products quality/mg)/(lignin quality/mg). The liquid product contains alcohols (monohydric alcohols such as butanol, butenol, hexyl alcohol, 2-hexenol, 2-ethyl butanol, 2-methyl pentenol), esters (ethyl acetate, butyl acetate, ethyl butyrate, ethyl hexanoate, ethyl 3-hexenoate, ethyl 2-hexenoate, ethyl 3-methylpentanoate, ethyl 4-octanoate, ethyl octanoate), phenols (guaiacol, 4-methyl guaiacol, 4-ethyl guaiacol, 4-propyl guaiacol), benzyl alcohols (benzyl alcohol, 2-methyl benzyl alcohol, 4-ethyl benzyl alcohol, 2,4,5-trimethyl benzyl alcohol) and arenes (toluene, xylene, 3-methyl ethylbenzene, 2,4-dimethyl ethylbenzene, 2,5-dimethyl ethylbenzene)

Example 2-6

Performance comparison of $Mo_2N/Al_2O_3$, $Mo_2N$/NaY and $Mo_2N/SiO_2$ is shown in the following table. The reaction process is the same as in example 2-5. The maximum product yield appeared when $Mo_2N/Al_2O_3$ was used, which indicates that alumina is the preferable catalyst support.

| Catalysts | Yield of alcohols | Yield of esters | Yield of phenols | Yield of benzyl alcohols | Yield of arenes |
|---|---|---|---|---|---|
| $Mo_2N/Al_2O_3$ | 108.7 | 589.3 | 21.3 | 81.4 | 64.1 |
| $Mo_2N$/NaY | 30.7 | 337.1 | 27.4 | 29.9 | 34.0 |
| $Mo_2N/SiO_2$ | 22.4 | 255.0 | 8.4 | 19.1 | 61.1 |

Example 2-7

Performance comparison of catalysts prepared at different temperatures is shown in the following table. The reaction process is the same as in example 2-5. It is evident that all the $Mo_2N/Al_2O_3$ synthesized at these temperatures performed well resulting in high product yields, while the highest total product yield is attributed to Mo$_2$N/Al$_2$O$_3$ obtained at 700° C.

| Nitration Temperature/° C. | Yield of alcohols | Yield of esters | Yield of phenols | Yield of benzyl alcohols | Yield of arenes |
|---|---|---|---|---|---|
| 600 | 81.2 | 523.7 | 24.3 | 59.6 | 75.8 |
| 650 | 108.7 | 589.3 | 21.3 | 81.4 | 64.1 |
| 700 | 149.0 | 759.2 | 31.8 | 154.4 | 90.5 |
| 750 | 109.3 | 573.6 | 27.0 | 117.4 | 77.9 |

Example 2-8

Performance comparison of the catalysts with Mo content of 10%, 20%, 30%, 46 wt. % is shown in the following table. The reaction process is the same as in example 2-5. As the data show that pure alumina has a low catalytic activity in the reaction and the total product yield rises in the first stage and then decreases as the Mo content increases. The total yield is almost the same when the Mo content is 20 wt. % and 30 wt. % and also the most. The yields of esters, phenols, benzyl alcohols and arenes are consistent with the total yield while the alcohol yield goes down as the Mo content increases.

| Mo content wt. % | Yield of alcohols | Yield of esters | Yield of phenols | Yield of benzyl alcohols | Yield of arenes |
|---|---|---|---|---|---|
| 0 | 51.6 | 141.4 | 14.5 | 58.1 | 26.0 |
| 10 | 497.4 | 494.8 | 5.4 | 11.4 | 45.3 |
| 20 | 143.1 | 831.1 | 27.2 | 93.7 | 88.7 |
| 30 | 149.0 | 759.2 | 31.8 | 154.4 | 90.5 |
| 47 | 59.6 | 481.2 | 26.9 | 72.1 | 88.0 |

Example 2-9

The comparison of product yields obtained at different reaction temperature is shown in the following table. The reaction process is the same as in example 2-5, with the exception of the reaction temperature.

| Reaction Temperature/° C. | Yield of alcohols | Yield of esters | Yield of phenols | Yield of benzyl alcohols | Yield of arenes |
|---|---|---|---|---|---|
| 270 | 39.8 | 395.0 | 10.1 | 50.4 | 73.9 |
| 280 | 149.0 | 759.2 | 31.8 | 154.4 | 90.5 |
| 290 | 154.8 | 804.1 | 49.2 | 133.0 | 117.0 |
| 300 | 146.8 | 770.8 | 46.2 | 65.6 | 110.9 |

The Third Group of Examples: Decomposition of Lignin with WP and MoP Catalysts

Example 3-1

For a typical preparation, alumina was impregnated with the solution of diammonium hydrogen phosphate and ammonium meta-tungstate, then the mixtures were dried at 120° C. for 12 h and calcined at 500° C. for 4 h. The precursor was finally reduced at flowing hydrogen atmosphere, and the obtained catalyst was WP/Al$_2$O$_3$ with the W content was 29 wt. %. The temperature programmed reduction was set by heating from room temperature to 300° C., and then from 300° C. to 650° C. at a rate of 1° C./min and finally held at 650° C. for 120 min. The unsupported WP catalyst was prepared by evaporation of the water in a solution of diammonium hydrogen phosphate and ammonium meta-tungstate, then dried and reduced under flowing hydrogen atmosphere.

Example 3-2

The same catalyst synthesis process was employed as in example 3-1, with the exception of the W content. The content of W in the WP/Al$_2$O$_3$ catalyst was set as 1 wt. %, 5 wt. %, 10 wt. %, 15 wt. %, 20 wt. %, 30 wt. % and 50 wt. %.

Example 3-3

The same catalyst synthesis process was employed as in example 3-1, with the exception that the catalyst support was changed from alumina to SiC, SiO$_2$ and AC. Tungsten phosphide catalysts with different supports were obtained.

Example 3-4

Placing a certain amount of the diammonium hydrogen phosphate, nickel nitrate and ammonium meta-tungstate into water. After having dissolved well, the solution is then used to impregnate the Al$_2$O$_3$ support, then dried at 120° C. for 12 h and calcined at 500° C. for 4 h, and finally reduced under the flowing hydrogen atmosphere. The temperature programmed reduction was set by heating from room temperature to 300° C., and then from 300° C. to 650° C. at a rate of 1° C./min and held at 650° C. for 120 min. Finally the Ni-WP/Al$_2$O$_3$ catalyst was obtained with the Ni content of 2 wt. % (2 wt. % Ni-20 wt % WP/Al$_2$O$_3$). By changing the promoter Ni to other metals like Fe, Co, Cu and Cr, Fe-WP/Al$_2$O$_3$, Co-WP/Al$_2$O$_3$, Cu-WP/Al$_2$O$_3$ and Cr-WP/Al$_2$O$_3$ catalysts are also obtained.

Example 3-5

The same catalyst synthesis process was employed as in example 3-4, with the exception that the catalyst support was changed from alumina to SiC, SiO$_2$ and AC.

Example 3-6

The same catalyst synthesis process was employed as in example 3-4, with the exception that the metal load was changed. The loading W percent in the Ni-WP/Al$_2$O$_3$ catalyst was 1 wt. %, 5 wt. %, 15 wt. %, 30 wt. % and 50 wt. %, respectively.

Example 3-7

The same catalyst synthesis process was employed as in example 3-4, with the exception of changing the weight percentage of the promoter. Different catalysts were prepared containing 1 wt. % Ni-WP/Al$_2$O$_3$, 5 wt. % Ni-WP/Al$_2$O$_3$, 10 wt. % Ni-WP/Al$_2$O$_3$, 0.1 wt. % Fe-WP/Al$_2$O$_3$, 5 wt. % Fe-WP/Al$_2$O$_3$, 15 wt. % Fe-WP/Al$_2$O$_3$, 3 wt. % Cu-WP/Al$_2$O$_3$, 8 wt. % Cu-WP/Al$_2$O$_3$, 12 wt % Cu-WP/Al$_2$O$_3$, 3 wt. % Co-WP/Al$_2$O$_3$, 8 wt. % Co-WP/Al$_2$O$_3$, 10 wt. % Co-WP/Al$_2$O$_3$, 2 wt. % Cr-WP/Al$_2$O$_3$, 6 wt. % Cr-WP/Al$_2$O$_3$, 12 wt. % Cr-WP/Al$_2$O$_3$.

Example 3-8

According to the catalyst synthesis process of examples 3-4 through 7, MoP catalysts were synthesized. For a typical preparation, alumina was impregnated with the solution of diammonium hydrogen phosphate, nickel nitrate and ammonium molybdate, then the mixtures were dried at 120° C. for 12 h and calcined at 500° C. for 4 h. The precursor was finally reduced under flowing hydrogen atmosphere, and the temperature program for the reduction was set by heating from room temperature to 300° C., and then from 300° C. to 650° C. at a rate of 1° C./min and finally held at 650° C. for 120 min. The obtained catalyst was 2 wt. % Ni-20 wt. % MoP/Al$_2$O$_3$.

Example 3-9

Support was changed to SiC, SiO2 and AC, and the metal content and the promoter content were also changed. The obtained catalysts contain 1 wt. % Ni-MoP/Al$_2$O$_3$, 5 wt. % Ni-MoP/Al$_2$O$_3$, 10 wt. % Ni-MoP/Al$_2$O$_3$, 0.1 wt. % Fe-MoP/Al$_2$O$_3$, 5 wt. % Fe-MoP/Al$_2$O$_3$, 15 wt. % Fe-MoP/Al$_2$O$_3$, 3 wt. % Cu-MoP/Al$_2$O$_3$, 8 wt. % Cu-MoP/Al$_2$O$_3$, 12 wt. % Cu-MoP/Al$_2$O$_3$, 3 wt. % Co-MoP/Al$_2$O$_3$, 8 wt. % Co-MoP/Al$_2$O$_3$, 10 wt. % Co-MoP/Al$_2$O$_3$, 2 wt. % Cr-MoP/Al$_2$O$_3$, 6 wt. % Cr-MoP/Al$_2$O$_3$, 12 wt. % Cr-MoP/Al$_2$O$_3$.

Example 3-10

The prepared catalysts were transferred to the batch reactor which was loaded with 1.00 g Kraft lignin, 50 mL water and 50 mL ethanol. The initial gas pressure was 2 MPa of hydrogen. After reaction for 2 h at a set temperature of 280° C., the system was cooled to room temperature. After releasing the gas, the reaction mixture was filtrated and analyzed. The liquid products were qualitatively analyzed with GC-MS (Agilent GC6890-MS5973), and quantitatively analyzed with GC (Agilent GC6890 with a FID) with internal standard method. The columns used with the FID and MS detector were both HP-5MS capillary columns (30 m×0.25 mm×0.25 μm). The yield of liquid products was expressed as mg/g lignin.

Example 3-11

The reaction process was the same as employed in example 3-10, with the exception of changing the initial gas to 2 MPa N$_2$. The results were as follows.

| Initial gas | Monophenols yield (mg/g lignin) |
|---|---|
| H$_2$ 2 MPa | 49.5 |
| N$_2$ 2 MPa | 54.5 |

Example 3-12

The reaction process was the same as employed in example 3-10, with the exception of changing the support of the catalysts. The results were as follows.

| Catalyst | Monophenols yield (mg/g lignin) |
|---|---|
| WP/SiC | 39.5 |
| WP/SiO$_2$ | 36.5 |
| WP/Al$_2$O$_3$ | 49.5 |
| WP/AC | 67.6 |

Example 3-13

The reaction process was the same as employed in example 3-10, with the exception of changing the catalysts to the catalysts with 2 wt % promoter. The results were as follows.

| Catalyst | Monophenols yield (mg/g lignin) |
|---|---|
| Fe—WP/Al$_2$O$_3$ | 39.5 |
| Co—WP/Al$_2$O$_3$ | 35.8 |
| Ni—WP/Al$_2$O$_3$ | 34.5 |
| Cu—WP/Al$_2$O$_3$ | 33.7 |
| Cr—WP/Al$_2$O$_3$ | 48.5 |

Example 3-14

The reaction process was the same as employed in example 3-10, with the exception of changing the catalysts to the MoP catalysts with 2 wt. % promoter. The results were as follows.

| Catalyst | Monophenols yield (mg/g lignin) |
|---|---|
| Fe—MoP/Al$_2$O$_3$ | 61.0 |
| Co—MoP/Al$_2$O$_3$ | 58.5 |
| Ni—MoP/Al$_2$O$_3$ | 56.3 |
| Cu—MoP/Al$_2$O$_3$ | 56.0 |
| Cr—MoP/Al$_2$O$_3$ | 63.2 |

Example 3-15

The reaction process was the same as employed in example 3-10, with the exception of changing the catalysts. The results were as follows.

| Catalyst | Monophenols yield (mg/g lignin) |
|---|---|
| Ni—MoP/Al$_2$O$_3$ | 56.3 |
| Ni—MoP/AC | 64.5 |
| Ni—MoP/SiO$_2$ | 50.5 |
| Ni—WP/Al$_2$O$_3$ | 34.5 |
| Ni—WP/AC | 56.5 |
| Ni—WP/SiO$_2$ | 35.5 |

Example 3-16

The reaction process was the same as employed in example 3-10, with the exception of changing the metal content of the catalysts. The results were as follows.

| Catalyst | Monophenols yield (mg/g lignin) |
|---|---|
| 10 wt. % WP/Al$_2$O$_3$ | 22.5 |
| 15 wt. % WP/Al$_2$O$_3$ | 38.0 |
| 20 wt. % WP/Al$_2$O$_3$ | 49.5 |
| 30 wt. % WP/Al$_2$O$_3$ | 51.0 |

Example 3-17

The reaction process was the same as employed in example 3-10, with the exception of changing the promoter content of the catalysts. The results were as follows.

| Catalyst | Monophenols yield (mg/g lignin) |
|---|---|
| 1 wt. % Ni—WP/Al$_2$O$_3$ | 38.5 |
| 2 wt. % Ni—WP/Al$_2$O$_3$ | 34.5 |
| 5 wt. % Ni—WP/Al$_2$O$_3$ | 31.0 |
| 1 wt. % Ni—MoP/Al$_2$O$_3$ | 62.5 |
| 2 wt. % Ni—MoP/Al$_2$O$_3$ | 56.3 |
| 5 wt. % Ni—MoP/Al$_2$O$_3$ | 54.5 |

Example 3-18

The reaction process was the same as employed in example 3-10, with the exception of changing the reactive solvent. The results were as follows.

| Catalyst | Solvent | Monophenols yield (mg/g lignin) |
|---|---|---|
| WP/Al$_2$O$_3$ | EtOH | 30.5 |
| WP/Al$_2$O$_3$ | EtOH/H$_2$O (v:v = 4:1) | 33.2 |
| WP/Al$_2$O$_3$ | EtOH/H$_2$O (v:v = 1) | 49.5 |

Example 3-19

The reaction process was the same as employed in example 3-10, with the exception of changing the reaction time. The results were as follows.

| Catalyst | Reaction time (h) | Monophenols yield (mg/g lignin) |
|---|---|---|
| WP/Al$_2$O$_3$ | 2 | 49.5 |
| WP/Al$_2$O$_3$ | 3 | 44.3 |
| WP/Al$_2$O$_3$ | 6 | 37.0 |

Example 3-20

The reaction process was the same as employed in example 3-10, with the exception of changing the initial hydrogen pressure. The results were as follows.

| Catalyst | Initial pressure (MPa) | Monophenols yield (mg/g lignin) |
|---|---|---|
| WP/Al$_2$O$_3$ | 1 | 51.4 |
| WP/Al$_2$O$_3$ | 2 | 49.5 |
| WP/Al$_2$O$_3$ | 3 | 46.4 |
| WP/Al$_2$O$_3$ | 4 | 39.7 |

The Fourth Group of Examples: Decomposition of Lignin with Amorphous Alloy Catalysts Example 4-1

3.5 g ammonia paramolybdate was dissolved in 20 mL of aqueous ammonia. Then 4 g activated carbon was added into the solution and impregnated for 10 min. Then the solution was evaporated so as to dry slowly at 70° C. The solid was dried for 12 h at 120° C. and then dried for 2 h at 200° C. The prepared material was the catalyst precursor. 1.5 g NaBH$_4$ was dissolved in 20 mL water. The precursor was reduced by adding 2 mL/min NaBH$_4$ solution under stirring in an ice-water bath. When the reaction was completed, the catalyst was filtrated and washed to pH=7 and then washed with ethanol. Finally, the catalyst was kept in ethanol. The as prepared catalyst was denoted by Mo-B/AC.

Example 4-2

3.5 g ammonia paramolybdate was dissolved in 20 mL of aqueous ammonia. Then 4 g activated carbon was added into the solution and impregnated for 10 min. Then the solution was evaporated so as to dry slowly at 70° C. The solid was dried for 12 h at 120° C. and then dried for 2 h at 200° C. The prepared material was the catalyst precursor. 1.5 g NaPO$_2$ was dissolved in 20 mL water. The precursor was reduced by adding 2 mL/min NaPO$_2$ solution under stirring in ice-water bath. When the reaction was completed, the catalyst was filtrated and washed to pH=7 and then washed with ethanol. Finally, the catalyst was kept in ethanol. The as prepared catalyst was denoted by Mo-P/AC.

Example 4-3

The preparation method used is similar to that used in example 4-1. However, the concentrations of ammonia paramolybdate and NaBH$_4$ change proportionally. The Mo loading was 1 wt. %, 5 wt. %, 10 wt. %, 15 wt. %, 20 wt. %, 30 wt. % for Mo-B/AC respectively. These catalysts were denoted by 1 wt. %, 5 wt. %, 10 wt. %, 15 wt. %, 20 wt. %, 30 wt. % Mo-B/AC, respectively.

Example 4-4

The preparation method used is similar to that used in example 4-1. However, the support is AC, Al$_2$O$_3$, SiO$_2$, SiC, TiO$_2$, MgO, respectively. These catalysts were denoted by Mo—B/AC, Mo—B/Al2O$_3$, Mo—B/SiO$_2$, Mo—B/SiC, Mo—B/TiO$_2$, Mo—B/MgO.

Example 4-5

3.5 g ammonia paramolybdate was dissolved in 20 mL of aqueous ammonia. 1.5 g NaBH$_4$ was dissolved in 20 mL water. Then the ammonia paramolybdate solution was added into aqueous NaBH$_4$ at a 2 mL/min rate under stirring. When the reaction was completed, the solution was filtrated and the filter cake was washed with water. The as prepared catalyst was denoted by Mo—B amorphous alloy.

Example 4-6

3.5 g ammonia paramolybdate and 0.3 g Y (Y=Ni(NO$_3$)$_2$, Co(NO$_3$)$_2$, Fe(NO$_3$)$_3$, NaWO$_4$, K$_2$Cr$_2$O$_4$, K$_2$RuCl$_5$) was dissolved in 20 mL of aqueous ammonia. 1.5 g NaBH$_4$ was dissolved in 20 mL water. Then the solution of ammonia paramolybdate and Y was added into aqueous NaBH$_4$ at a 2 mL/min rate under stirring. When the reaction was completed, the solution was filtrated and the filter cake was washed with water. The as prepared catalyst was denoted by Mo—B—X (X represents the metal element in Y) amorphous alloy.

Example 4-7

3.5 g ammonia paramolybdate and 0.3 g Y (Y=Ni(NO$_3$)$_2$, Co(NO$_3$)$_2$, Fe(NO$_3$)$_3$, NaWO$_4$, K$_2$Cr$_2$O$_4$, K$_2$RuCl$_5$) was dissolved in 20 mL of aqueous ammonia. Then 4 g activated carbon was added into the solution and impregnated for 10 min. Then the solution was evaporated so as to dry slowly at 70° C. The solid was dried for 12 h at 120° C. and then dried for 2 h at 200° C. The prepared material was the catalyst precursor. 1.5 g $NaBH_4$ was dissolved in 20 mL water. The precursor was reduced by adding 2 mL/min $NaBH_4$ solution under stirring in an ice-water bath. When the reaction was completed, the catalyst was filtrated and washed to pH=7 and then washed with ethanol. Finally, the catalyst was kept in ethanol. The as prepared catalyst was denoted by Mo—B—X/AC amorphous alloy.

Example 4-8

The prepared catalysts were transferred to the batch reactor which was loaded with 1.00 g Kraft lignin, 50 mL water and 50 mL ethanol. The initial gas pressure was 2 MPa of hydrogen. After reaction for 2 h at a temperature of 280° C., the system was cooled to room temperature. After releasing the gas, the reaction mixture was filtrated and analyzed. The liquid products were qualitatively analyzed with GC-MS (Agilent GC6890-MS5973), and quantitatively analyzed with GC (Agilent GC6890 with a FID) with an internal standard method. The columns used with the FID and MS detector were both HP-5MS capillary columns (30 m×0.25 mm×0.25 μm). The yield of liquid products was expressed as mg/g lignin.

Example 4-9

The products of lignin conversion reactions with doped Mo-B/AC catalyst are as follows. The reaction conditions are the same as those employed in example 4-8. As shown in the table, Mo—B—X/AC is active for lignin conversion. Mo-B/AC shows the highest activity.

| Catalyst | Yield of alcohols | Yield of esters | Yield of Phenols | Yield of Benzyl alcohols | Yield of Arenes |
|---|---|---|---|---|---|
| Mo—B/AC | 55 | 720 | 19 | 6 | 220 |
| Mo—B—Ni/AC | 36 | 549 | 17 | 9 | 204 |
| Mo—B—Co/AC | 30 | 470 | 13 | 14 | 196 |
| Mo—B—Fe/AC | 21 | 334 | 19 | 8 | 226 |
| Mo—B—W/AC | 12 | 255 | 21 | 11 | 143 |
| No catalyst | 5 | 27 | 18 | — | — |
| Mo—P/AC | 48 | 663 | 22 | 18 | 179 |

Example 4-10

The products of lignin conversion reactions with Mo-B/AC, Mo-B/$Al_2O_3$, Mo-B/$SiO_2$, Mo-B/SiC, Mo—B as the catalysts are given as follows. The reaction conditions are the same as those employed in example 4-8. As shown in the table, supported Mo—B is more active than unsupported Mo—B. Catalyst with AC support shows the highest yield.

| Catalyst | Yield of alcohols | Yield of esters | Yield of Phenols | Yield of Benzyl alcohols | Yield of Arenes |
|---|---|---|---|---|---|
| Mo—B/AC | 5.5 | 72.0 | 1.9 | 0.6 | 22.0 |
| Mo—B/$Al_2O_3$ | 4.0 | 75.6 | 1.2 | 0.2 | 19.3 |
| Mo—B/$SiO_2$ | 4.6 | 64.3 | 0.6 | 0.5 | 9.3 |
| Mo—B/SiC | 3.2 | 50.9 | 2.2 | 1.1 | 7.8 |
| Mo—B | 4.3 | 69.0 | 1.5 | 0.4 | 23.0 |

Example 4-11

The products of lignin conversion reactions with 30 wt. % Mo-B/AC, 20 wt. % Mo-B/AC, 10 wt. % Mo-B/AC as catalysts are listed as follows. The reaction conditions are the same as those employed in example 4-8. As shown in the table, Mo-B/AC with different Mo loading shows good activity. 20 wt. % Mo-B/AC shows the highest yield.

| Catalyst | Yield of alcohols | Yield of esters | Yield of Phenols | Yield of Benzyl alcohols | Yield of Arenes |
|---|---|---|---|---|---|
| 30 wt. % Mo—B/AC | 52 | 693 | 15 | 7 | 235 |
| 20 wt. % Mo—B/AC | 55 | 720 | 19 | 6 | 220 |
| 10 wt. % Mo—B/AC | 32 | 484 | 16 | 6 | 194 |
| 5 wt. % Mo—B/AC | 30 | 306 | 14 | 5 | 181 |

Example 4-12

The products of lignin conversion reactions with Mo-B/AC as the catalyst in different solvents are given as follows. The reaction conditions are the same as those employed in example 4-8, with the exception of the solvent used. As shown in the table, water has the best selectivity for phenols, while ethanol gives the highest yield.

| Solvent | Yield of alcohols | Yield of esters | Yield of Phenols | Yield of Benzyl alcohols | Yield of Arenes |
|---|---|---|---|---|---|
| Water | — | 2 | 24 | — | — |
| Water/Ethanol (v:v = 1:1) | 12 | 135 | 17 | 1 | — |
| Ethanol | 55 | 720 | 19 | 6 | 220 |

Example 4-13

The products of lignin conversion reactions with Mo-B/AC as the catalyst under different hydrogen pressures. Reaction conditions are the same as those employed in example 4-8, with the exception of the hydrogen pressure.

| Initial hydrogen pressure (MPa) | Yield of alcohols | Yield of esters | Yield of Phenols | Yield of Benzyl alcohols | Yield of Arenes |
|---|---|---|---|---|---|
| 0 | 54 | 743 | 23 | 5 | 203 |
| 1 | 86 | 562 | 25 | 6 | 126 |
| 2 | 97 | 553 | 18 | 4 | 119 |
| 3 | 82 | 509 | 9 | 13 | 125 |
| 4 | 61 | 268 | 9 | 4 | 101 |

Example 4-14

The products of lignin conversion reactions with Mo-B/AC catalysts with different reaction times. The reaction conditions are the same as those employed in example 4-8, with the exception of the reaction time.

| Reaction time (h) | Yield of alcohols | Yield of esters | Yield of Phenols | Yield of Benzyl alcohols | Yield of Arenes |
|---|---|---|---|---|---|
| 0.5 | 3 | 59 | 9 | 1 | 12 |
| 2 | 38 | 796 | 43 | 3 | 136 |

-continued

| Reaction time (h) | Yield of alcohols | Yield of esters | Yield of Phenols | Yield of Benzyl alcohols | Yield of Arenes |
|---|---|---|---|---|---|
| 4 | 47 | 748 | 27 | 6 | 275 |
| 6 | 43 | 690 | 15 | 4 | 230 |

Example 4-15

The products of lignin conversion reactions with Mo-B/AC as the catalyst under different atmospheres. The reaction conditions are the same as those employed in example 4-8, with the exception of the atmosphere.

| Gas atmosphere | Yield of alcohols | Yield of esters | Yield of Phenols | Yield of Benzyl alcohols | Yield of Arenes |
|---|---|---|---|---|---|
| $H_2$-0 MPa | 48 | 659 | 14 | 4 | 168 |
| $N_2$-0 MPa | 55 | 720 | 19 | 6 | 220 |

Example 4-16

The products of lignin conversion reactions with Mo-B/AC catalysts under 0 MPa $N_2$ with different reaction times. The reaction conditions are the same as those employed in example 4-8, with the exception of the reaction time and $N_2$ atmosphere.

| Reaction time (h) | Yield of alcohols | Yield of esters | Yield of Phenols | Yield of Benzyl alcohols | Yield of Arenes |
|---|---|---|---|---|---|
| 0.5 | 12 | 129 | 1 | 1 | 42 |
| 2 | 27 | 357 | 7 | 4 | 121 |
| 4 | 35 | 479 | 26 | 12 | 193 |
| 6 | 55 | 720 | 19 | 6 | 220 |

In the examples mentioned above, Klason lignin, milled wood lignin, enzymatic hydrolysis lignin, organosolv lignin can be used as feedstock to produce alcohols, esters, phenols, benzyl alcohols and arenes. The mass ratio of the lignin and solvent is 1:200-1:10, and a preferred range is 1:100-1:80. The mass ratio of the lignin and catalyst is 1:1-200:1, and a preferred range is 10:1-100:1. The reaction temperature is 250-350° C., and a preferred range is 260-300° C. The stirring rate is 100-1500 r/min.

The invention claimed is:

1. A process for the production of organic chemicals and fuels from lignin, comprising
   mixing the lignin with a molybdenum based catalyst and a solvent in a sealed reactor,
   introducing an inert gas to the reactor to replace oxygen therein, and
   heating the sealed reactor to perform a depolymerization reaction at a reaction temperature of 230-350° C. for 0.5-12 h to obtain liquid products comprising alcohols, esters, monophenols, benzyl alcohols and arenes;
   wherein the solvent is selected from the group consisting of deionized water, ethanol and a mixture of deionized water and ethanol;
   wherein the molybdenum based catalyst is a supported or an unsupported catalyst comprising molybdenum as an active metal;
   wherein the supported catalyst is expressed as $A_xB_y/C$, wherein A represents molybdenum which has a loading amount of 1-80 wt. % of the supported catalyst, B represents carbon, phosphorus or nitrogen, and C represents the support of the catalyst selected from the group consisting of aluminum oxide ($Al_2O_3$), activated carbon (AC), silicon dioxide ($SiO_2$), silicon carbide (SiC), zeolites and nano-carbon fiber, $0<x\leq2$ and $0<y\leq3$;
   wherein the unsupported catalyst is expressed as $A_xB_y$, wherein A represents molybdenum, B represents carbon, phosphorus or nitrogen, $0<x\leq2$, and $0<y\leq3$;
   wherein the lignin includes alkali lignin, Klason lignin, milled wood lignin and organosolv lignin;
   wherein the inert gas is nitrogen, argon or helium; and
   wherein the mixture of deionized water and ethanol comprises 10-50% of ethanol by volume.

2. The process of claim 1, wherein the sealed reactor is adapted to receive both liquid and solid or slurry feeds, and continuous distillation is used to maintain continuous reaction.

3. The process of claim 1, wherein,
   a mass ratio of the lignin and solvent is 1:200-1:10;
   a mass ratio of the lignin and catalyst is between 1:1 and 200:1;
   the sealed reactor has an initial reaction pressure of 0-6 MPa at room temperature of 20-25° C., and
   the reaction proceeds at 260-300° C. for 2-6 h under a stirring rate of 100-1500 r/min.

4. The process of claim 3, wherein the mass ratio of the lignin and solvent is 1:100-1:80.

5. The process of claim 3, wherein the mass ratio of the lignin and catalyst is between 10:1 and 100:1.

6. The process of claim 1, wherein the catalyst further comprises a promoter Z which has a loading amount of 0.1-15 wt. % of the catalyst and is selected from the group consisting of Fe, Ni, Co, Ru, W, Cu, Cr and Pt.

* * * * *